United States Patent
Usrey (10) Patent No.: US 12,201,732 B2
(45) Date of Patent: Jan. 21, 2025

(54) TRANSDERMAL PATCHES FOR HANGOVER MINIMIZATION AND/OR RECOCERY, AND/OR SLEEP IMPROVEMENT

(71) Applicant: GameChanger Patch Co., Dallas, TX (US)

(72) Inventor: Christoper Usrey, Dallas, TX (US)

(73) Assignee: GAME CHANGER PATCH CO., Dallas, TX (US)

( * ) Notice: Subject to any disclaimer, the term of this patent is extended or adjusted under 35 U.S.C. 154(b) by 9 days.

(21) Appl. No.: 17/558,179

(22) Filed: Dec. 21, 2021

(65) Prior Publication Data

US 2022/0193001 A1     Jun. 23, 2022

Related U.S. Application Data (60) Provisional application No. 63/130,367, filed on Dec. 23, 2020.

(51) Int. Cl.
*A61K 9/70*           (2006.01)
*A61K 45/06*       (2006.01)

(52) U.S. Cl.
CPC .......... *A61K 9/7092* (2013.01); *A61K 9/7053* (2013.01); *A61K 45/06* (2013.01)

(58) Field of Classification Search
CPC ... A61K 38/063; A61K 9/7038; A61K 31/185
See application file for complete search history.

(56) References Cited

U.S. PATENT DOCUMENTS

2011/0086086 A1 *   4/2011   Johnson ................. A61P 25/08
                                                   514/250
2016/0067102 A1 *   3/2016   Cotton ............. A61F 13/00059
                                                   602/46

FOREIGN PATENT DOCUMENTS

WO    WO-2012027603 A2 *   3/2012   ............. A61K 31/13
WO    WO-2020247961 A1 *   12/2020  ............. A61K 31/12

OTHER PUBLICATIONS

Lee et al., Regional Variation of Human Skin Surface Temperature, 2018, Ann Dermatol, 31(3), 349-352, DOI: 10.5021/ad.2019.31.3.349 (Year: 2018).*
Hangover Cure "Rebound Patch Review—Does it help reduce hangover symptoms?" (https://hangovercure.org/hangover-patches/rebound-patch-review/; accessed Apr. 18, 2023; updated Jun. 15, 2020) (Year: 2020).*

* cited by examiner

*Primary Examiner* — Mark V Stevens
(74) *Attorney, Agent, or Firm* — Williams Morgan, P.C.

(57) ABSTRACT

I disclose a patch, comprising a film having a first surface and a second surface, wherein the second surface is opposed to the first surface, and a coating on the first surface of the film, wherein the coating comprises a transdermal adhesive and one or more active ingredients. The active ingredient(s) may minimize and/or improve recovery from a hangover. I also disclose methods of using such patches; kits comprising such patches and instructions for their use; and methods of manufacturing such patches.

4 Claims, 5 Drawing Sheets

TRANSDERMAL PATCHES FOR HANGOVER MINIMIZATION AND/OR RECOCERY, AND/OR SLEEP IMPROVEMENT

BACKGROUND OF THE INVENTION

Field of the Invention

Generally, the present disclosure relates to transdermal patches for hangover minimization and/or recovery, and/or sleep improvement.

Description of the Related Art

Hangovers are the bane of drinkers of all types of alcoholic beverages. Though not to be bound by theory, one or more of acetaldehyde accumulation, changes in the immune system and glucose metabolism, dehydration, metabolic acidosis, disturbed prostaglandin synthesis, increased cardiac output, vasodilation, sleep deprivation, and malnutrition may lead to undesirable symptoms, such as headache, drowsiness, concentration problems, dry mouth, dizziness, fatigue, gastrointestinal distress (e.g., vomiting, diarrhea), absence of hunger, light sensitivity, depression, sweating, nausea, hyper-excitability, irritability, and anxiety. The ill effects of a hangover may also impair the person's ability to drive, operate complex equipment, or perform his or her job functions and/or personal and social obligations.

To address this problem, a number of oral supplements have been brought to market, each containing one or more compounds intended to counteract one or more of the biological effects of alcohol in a bid to diminish the number, intensity, and/or duration of hangover symptoms.

Though sometimes associated with excessive drinking, impaired sleep can afflict people for numerous reasons, including, but not necessarily limited to, stress, pain, discomfort, etc. A recent study estimates the overall cost of inadequate sleep in Australia at about US$1800 per capita per year, or about 6% of that country's GDP.[1] The person of ordinary skill in the art would expect the per capita annual cost of inadequate sleep to be comparable in any highly developed country in North America, Europe, Asia, or Oceania.

[1] https://pubmed.ncbi.nlm.nih.gov/29868785/

To address this problem, a number of oral supplements have been brought to market, each containing one or more compounds intended to improve sleep.

However, it remains desirable to find techniques, vehicles, and delivery avenues for improved hangover minimization and/or recovery, and/or sleep improvement.

SUMMARY OF THE INVENTION

The following presents a simplified summary of the disclosure in order to provide a basic understanding of some aspects of the disclosure. This summary is not an exhaustive overview of the disclosure. It is not intended to identify key or critical elements of the disclosure or to delineate the scope of the disclosure. Its sole purpose is to present some concepts in a simplified form as a prelude to the more detailed description that is discussed later.

In one embodiment, the present disclosure is directed to a patch, comprising a film having a first surface and a second surface, wherein the second surface is opposed to the first surface, and a coating on the first surface of the film, wherein the coating comprises a transdermal adhesive and one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract.

In one embodiment, the present disclosure is directed to a patch, comprising a film having a first surface and a second surface, wherein the second surface is opposed to the first surface, and a coating on the first surface of the film, wherein the coating comprises a transdermal adhesive and one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, sprouted peanut extract, ginger root extract, vitamin C, and magnesium malate.

In one embodiment, the present disclosure is directed to methods, comprising applying, to a skin area of a user, one or more patches, such as one or more of those briefly summarized above.

In one embodiment, the present disclosure is directed to kits, comprising one or more patches, such as one or more of those briefly summarized above, and instructions to perform a method, such as one or more of the methods briefly summarized above.

In one embodiment, the present disclosure is directed to a method, comprising dissolving, in an aqueous solution with a temperature from about 150° F. (about 65° C.) to about 212° F. (about 100° C.), one or more first active ingredients, to yield a first active ingredient solution; combining the first active ingredient solution with (a) one or more second active ingredient solutions, and (b) a transdermal adhesive, to yield a coating solution; coating the coating solution onto a first surface of a film, wherein the film has a first surface and a second surface, wherein the second surface is opposed to the first surface; applying a backer to the coating solution, to yield a roll of patches; and cutting the roll of patches, to yield a plurality of patches. The active ingredients may be those briefly summarized above.

The present disclosure may provide techniques, vehicles, and delivery avenues for improved hangover minimization and/or recovery, and/or improved sleep.

BRIEF DESCRIPTION OF THE DRAWINGS

The disclosure may be understood by reference to the following description taken in conjunction with the accompanying drawings, in which like reference numerals identify like elements, and in which.

For the avoidance of doubt, and consonant with United States Patent & Trademark Office practice, the drawings are not to scale.

While the subject matter disclosed herein is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION

Various illustrative embodiments of the disclosure are described below. In the interest of clarity, not all features of an actual implementation are described in this specification. It will, of course, be appreciated that, in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming but would be a routine undertaking for those of ordinary skill in the art having the benefit of this disclosure.

The present subject matter will now be described with reference to the attached figures. Various structures, systems and devices are conceptually depicted in the drawings for purposes of explanation only and to not obscure the present disclosure with details that are well known to those skilled in the art. Nevertheless, the attached drawings are included to describe and explain illustrative examples of the present disclosure. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

Embodiments herein are directed to transdermal patches for the minimization of and/or improved recovery from hangovers.

In one embodiment, the present disclosure relates to a patch, comprising a film having a first surface and a second surface, wherein the second surface is opposed to the first surface, and a coating on the first surface of the film, wherein the coating comprises a transdermal adhesive and one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract.

Figure 1A:
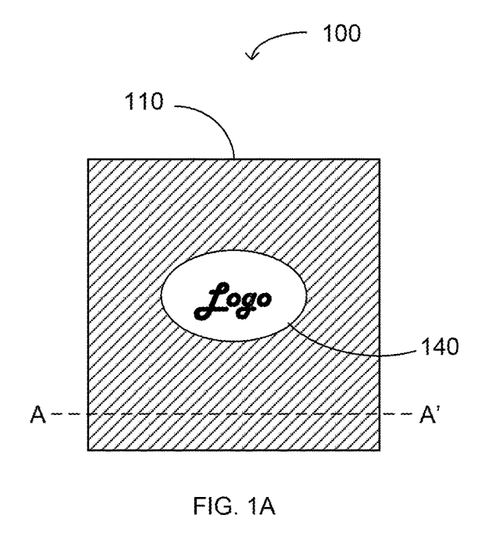
FIG. 1A presents a top view of a first patch, in accordance with embodiments herein.
Figure 1B:
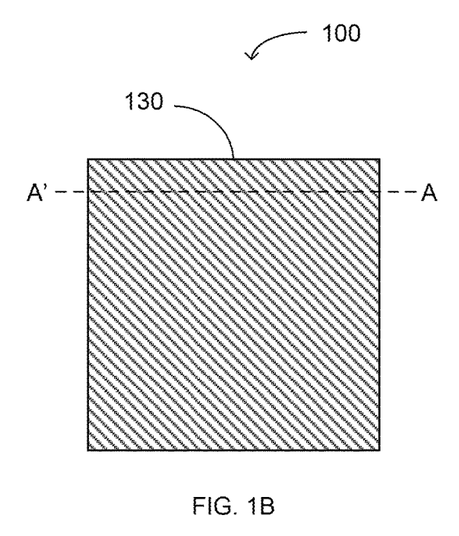
FIG. 1B presents a bottom view of the first patch, in accordance with embodiments herein.
Figure 1C:
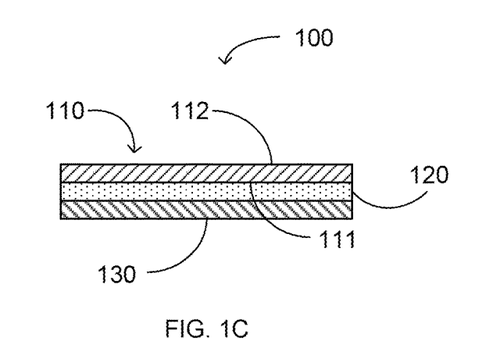
FIG. 1C presents a cross-sectional view, taken along the line A-A' in FIG. 1A and FIG. 1, of the first patch, in accordance with embodiments herein.

FIGS. 1A, 1, and 1C depict a first patch 100 in various views. FIG. 1A provides a top view of the first patch 100, FIG. 1B provides a bottom view of the first patch 100, and FIG. 1C provides a cross-section view of the first patch 100 taken along line A-A' in FIGS. 1A and 1B.

The first patch 100 comprises a film 110. By "film" is meant a flexible solid with a much smaller extent in a vertical direction (i.e., from the side of the first patch 100 shown in FIG. 1A to the opposite side of the first patch 100 shown in FIG. 1B) than in first and second orthogonal horizontal directions (i.e., the up-down and left-right directions of FIG. 1A and FIG. 1). Accordingly, as best seen in FIG. 1C, the film has a first surface 111 and a second surface 112, wherein the second surface 112 is opposed to the first surface 111

The film 110 may be transparent, translucent, or opaque.

The film 110 may be formed from any material(s) known to be suitable for making films and generally suitable for applications in proximity to human skin for a period of up to about 12 hours. In one embodiment, the film 110 comprises polyethylene. An exemplary polyethylene is clear FT-200 polyethylene with a thickness (viz., the average extent between the first surface 111 and the second surface 112) of about 0.102 mm (about 0.004 inches).

Alternatively or in addition, in one embodiment, the film 110 is substantially free of latex.

The first patch 100 also comprises a coating 120 on the first surface 111 of the film 110.

The coating 120 comprises a transdermal adhesive. Any adhesive known for transdermal use (i.e., for application to human skin with minimal side effects) may be used as the transdermal adhesive in the coating 120. Suitable transdermal adhesives are known to the person of ordinary skill in the art having the benefit of the present disclosure.

The coating 120 also comprises one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract.

Though not to be bound by theory, the active ingredients may have the following features.

Glutathione is the human body's master antioxidant that is very potent detoxifying agent for the liver and is critical to the breakdown and elimination of alcohol by the human body. As a person drink alcohol, glutathione stores are depleted. Oral supplementation is almost impossible because the human stomach metabolizes about 90+% in the "first pass"[2], rendering oral glutathione essentially useless for hangover remediation. Fat encapsulation of glutathione increases bioavailability, but has an extremely unpleasant, nauseating taste and smell, as well as an aftertaste and burps. This antioxidant also helps with alcohol flushing.

[2] https://pubmed.ncbi.nlm.nih.gov/6362950/

N-Acetyl Cysteine (NAC) is another powerful antioxidant that breaks down into glutathione and replenishes glutathione levels. NAC is the standard of care for the treatment of acetaminophen toxicity because of these abilities.[3] This increase in glutathione keeps breaking down alcohol metabolites that give a person hangover symptoms such as headaches and nausea.

[3] https://www.ncbi.nlm.nih.gov/pmc/articles/PMC3576299/

L-Cysteine is an essential amino acid which is required by the body for proper growth and functioning. A very small amount of it is naturally found in the body, so the requirement has to be met with the help of food and supplements. L-Cysteine binds with other amino acids, glutamine and glycine, to form a powerful antioxidant called glutathione that protects the liver, metabolizes alcohol and its toxic by-product acetaldehyde. L-cysteine has been shown in a recent study to mitigate hangover effects[4].

[4] https://pubmed.ncbi.nlm.nih.gov/32808029/

Alpha Lipoic Acid (ALA), an amino acid, is a potent, powerful antioxidant that helps the human body produce glutathione. ALA is essential in at least five enzyme systems involved in metabolism of alcohol. ALA counters hangover symptoms by reducing the body's acetaldehyde toxicity and inflammation.

Milk thistle is a prickly flowering plant that has been used for centuries as a hangover remedy because of its liver boosting properties. Milk thistle extract (silymarin) enhances hepatic glutathione and may contribute to the antioxidant defense of the liver. These activities of milk thistle extract (silymarin) are currently best understood to be caused by its ability to inhibit the free radicals that are produced from the metabolism of toxic substances such as alcohol, acetaminophen, and carbon tetrachloride, thus protecting the human liver.[5]

[5] https://www.ncbi.nlm.nih.gov/pmc/articles/PMC3959115/

L-Theanine, a non-protein amino acid found in green tea, may modulate aspects of brain function in humans, including inducing a sense of calm. It also accelerates the breakdown of alcohol metabolites and blocks free radicals from polluting the human body. L-Theanine also counteracts alcohol-induced glutathione depletion and allows the human body to produce natural anti-oxidants.

Taurine is a naturally-occurring amino acid that has been called a "wonder molecule"[6]. Studies show that taurine defends liver cells against free radicals and toxins, helping to reduce the severity of oxidative stress-induced liver injury.[7] In human studies, supplementation of taurine over a 3 month period was shown to repair liver damage as well as oxidative stress.[8] Finally, it helps hydrate a person at a cellular level[9], heals sore muscles, improves concentration, and improves the body's glucose tolerance to minimize the effects of sugar in alcohol and mixers.

[6] Yamori Y, Taguchi T, Hamada A, Kunimasa K, Mori H, Mori M. Taurine in health and diseases: consistent evidence from experimental and epidemiological studies. *J Biomed Sci.* 2010; 17 Suppl 1:S6.
[7] Miyazaki T, Bouscarel B, Ikegami T, Honda A, Matsuzaki Y. The protective effect of taurine against hepatic damage in a model of liver disease and hepatic stellate cells. *Adv Exp Med Biol.* 2009; 643:293-303.
[8] Hu Y H, Lin C L, Huang Y W, Liu P E, Hwang D F. Dietary amino acid taurine ameliorates liver injury in chronic hepatitis patients. *Amino Acids.* 2008 August; 35(2):469-73.
[9] https://pubmed.ncbi.nlm.nih.gov/12880428/

Quercetin, a bioflavonoid, is a powerful antihistamine and anti-inflammatory that neutralizes inflammation associated with the pain from a hangover.[10] It also boosts natural defenses by increasing the level and function of enzymes needed for glutathione synthesis in the body. Finally, it reduces buildup of acetaldehyde by improving alcohol metabolism. It may impart a yellow hue to the coating 120.

[10] https://www.ncbi.nlm.nih.gov/pmc/articles/PMC4808895/

Sweet lime extract and Korean pear extract are fruit extracts that enhance the activity of enzymes (ADH and ALDH) responsible for breaking down alcohol. The current scientific consensus is that polyphenols are responsible for this activity. In the study cited herein, both sweet lime and Korean pear were shown to enhance ALDH and ADH activities resulting in faster elimination of acetaldehyde[11]

[11] https://www.sciencedirect.com/science/article/pii/S266592711930005X#bib12

Sprouted peanut extract (SPE) is a phenolic compound with known antioxidant and anti-inflammatory properties that is also high in resveratrol. In addition, SPE has an antioxidant effect and stimulates the activity of detoxifying enzymes via Nrf2 activation in dermal fibroblasts. Several studies have demonstrated that phenolic compounds in SPE are responsible for various biological activities. Furthermore, the sprouting of peanuts results in abundant production of asparagine/aspartic acid, which may help relieve hangover after drinking ethanol. Moderate alcohol intake causes acute hangover because alcohol is generally degraded by ADH into acetaldehyde. Alcohol concentration in the blood is reduced over time because acetaldehyde is converted to acetate by ALDH, a direct detoxifying enzyme. SPE promotes alcohol elimination by increasing ADH and ALDH activities and removing alcohol from the blood.[12]

[12] https://www.ncbi.nlm.nih.gov/pmc/articles/PMC3999802/

Prickly pear is a species of cactus which has potent antioxidant and anti-inflammatory properties because it is high in polyphenols. Prickly pear extract was used in a hangover study in New Orleans. The researchers found that it had a moderate effect on reducing hangover symptoms, apparently by inhibiting inflammatory mediators.[13]

[13] https://jamanetwork.com/journals/jamainternalmedicine/fullarticle/217133

In one embodiment, the coating 120 may comprise two or more of the active ingredients.

In one embodiment, the coating 120 may comprise three or more of the active ingredients.

In one embodiment, the coating 120 may comprise four or more of the active ingredients.

In one embodiment, the coating 120 may comprise five or more of the active ingredients.

In one embodiment, the coating 120 may comprise six or more of the active ingredients.

In one embodiment, the coating 120 may comprise seven or more of the active ingredients.

In one embodiment, the coating 120 may comprise eight or more of the active ingredients.

In one embodiment, the coating 120 may comprise nine or more of the active ingredients.

In one embodiment, the coating 120 may comprise ten or more of the active ingredients.

In one embodiment, the coating 120 may comprise eleven of the active ingredients.

For each active ingredient included in the coating 120, the amount of the active ingredient may be determined and adjusted as a routine matter by the person of ordinary skill in the art having the benefit of the present disclosure.

In one embodiment, the coating 120 may comprise from 3 mg to 30 mg glutathione. Alternatively or in addition, the coating 120 may comprise from 2 mg to 20 mg NAC. Alternatively or in addition, the coating 120 may comprise from 2 mg to 20 mg L-cysteine. Alternatively or in addition, the coating 120 may comprise from 2 mg to 20 mg ALA. Alternatively or in addition, the coating 120 may comprise from 2 mg to 20 mg milk thistle extract. Alternatively or in addition, the coating 120 may comprise from 1.5 mg to 15 mg L-theanine. Alternatively or in addition, the coating 120 may comprise from 2 mg to 20 mg taurine. Alternatively or in addition, the coating 120 may comprise from 1.5 mg to 15 mg quercetin. Alternatively or in addition, the coating 120 may comprise from 0.5 mg to 6 mg sweet lime extract. Alternatively or in addition, the coating 120 may comprise from 0.5 mg to 6 mg Korean pear extract. Alternatively or in addition, the coating 120 may comprise and from 0.5 mg to 6 mg prickly pear extract.

In one particular embodiment, the coating may comprise 10 mg glutathione. Alternatively or in addition, in this particular embodiment, the coating 120 may comprise 6 mg NAC. Alternatively or in addition, in this particular embodiment, the coating 120 may comprise 6 mg L-cysteine.

Alternatively or in addition, in this particular embodiment, the coating 120 may comprise 6 mg ALA. Alternatively or in addition, in this particular embodiment, the coating 120 may comprise 6 mg milk thistle extract. Alternatively or in addition, in this particular embodiment, the coating 120 may comprise 5 mg L-theanine. Alternatively or in addition, in this particular embodiment, the coating 120 may comprise 6 mg taurine. Alternatively or in addition, in this particular embodiment, the coating 120 may comprise 5 mg quercetin. Alternatively or in addition, in this particular embodiment, the coating 120 may comprise 2 mg sweet lime extract. Alternatively or in addition, in this particular embodiment, the coating 120 may comprise 2 mg Korean pear extract. Alternatively or in addition, in this particular embodiment, the coating 120 may comprise and 2 mg prickly pear extract.

For the extracts set forth above, the amount in milligrams is the dry weight of the extract.

Optionally, the coating 120 may further comprise one or more penetration enhancers. The person of ordinary skill in the art will be aware that penetration enhancers are compounds that increase the uptake of another compound through human skin. The penetration enhancer may be an emulsifier. In one embodiment, the penetration enhancer(s) is/are selected from the group consisting of emulsifiers having a hydrophilic-lipophilic balance (HLB) value of at least 7, phosphatidylcholine, ethanol, oleic acid, propylene glycol, liposomes, vesicles, and two or more thereof.

In addition to the film 110 and the coating 120, the first patch 100 may further comprise one or more other features.

In one embodiment, the first patch 100 may further comprise a printed matter 140 on the second surface 112 of the film. The printed matter 140 may comprise text, graphics, or both. For example, the printed matter 140 may comprise a logo of a manufacturer of the first patch 100; an advertiser, such as a bar or tavern in which drinking alcoholic beverages may occur, a liquor store selling alcoholic beverages, a manufacturer of alcoholic beverages; etc.

In a particular embodiment, the printed matter 140 may comprise an ink which is substantially opaque at a temperature below about 80° F. (about 27° C.), e.g., at room temperature, and which is substantially transparent at a temperature above about 95° F. (about 35° C.), e.g., at human body temperature. A printed matter 140 comprising such an ink may provide the user of the first patch 100 and/or the user's companions with visible affirmation that the first patch 100 is transcutaneously delivering the active ingredient(s) to the user's body, by the disappearance of the printed matter 140 subsequent to adhering the first patch 100 to human skin at over about 98° F. (about 37° C.).

Alternatively or in addition, the first patch 100 may further comprise a backer 130 on the coating 120. Specifically, the backer 130 is disposed on the surface of the coating 120 opposite the film 110. The backer 130 may protect the coating 120 from removal from the film 110 and/or premature release of the active ingredient(s). If desired, the backer 130 may be configured for convenient manual removal from the coating 120 at a desired time, e.g., by comprising a tab extending laterally away from the main body of the first patch 100 for convenient pinching between the thumb and forefinger of a user and subsequent pulling; by being formed in two or more pieces around a seam(s) in which a fingernail or tweezers may find purchase to remove the pieces; etc. The backer 130 may be formed of coated paper or other material, which may be chosen as a routine matter by the person of ordinary skill in the art having the benefit of the present disclosure.

Regardless of what further components it may comprise, the first patch 100 may be waterproof, water-resistant, or neither waterproof nor water-resistant. Desirably, the first patch 100 may be sufficiently waterproof or water-resistant for the first patch 100 to remain adhered to a typical user's skin for a period of at least about 6 hours despite the user's sweat, exposure to liquids (e.g., spilled drinks, hot tubs, swimming pools, natural freshwater, natural saltwater, etc.), or the like.

In another embodiment, the present disclosure relates to a patch, comprising a film having a first surface and a second surface, wherein the second surface is opposed to the first surface, and a coating on the first surface of the film, wherein the coating comprises a transdermal adhesive and one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, sprouted peanut extract, ginger root extract, vitamin C, and magnesium malate.

Figure 2A:
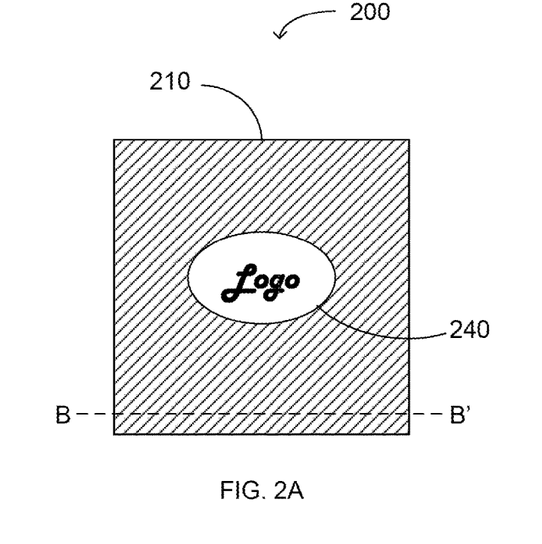
FIG. 2A presents a top view of a second patch, in accordance with embodiments herein.
Figure 2B:
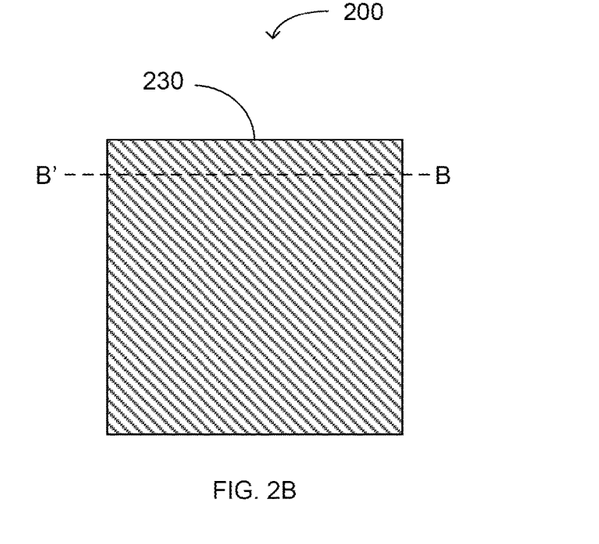
FIG. 2B presents a bottom view of the second patch, in accordance with embodiments herein.
Figure 2C:
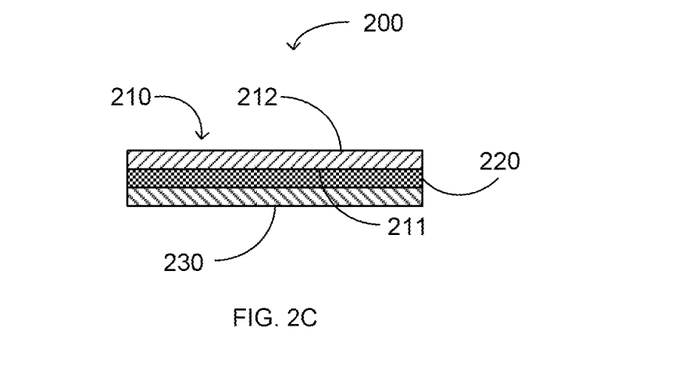
FIG. 2C presents a cross-sectional view, taken along the line B-B' in FIG. 2A and FIG. 2B, of the second patch, in accordance with embodiments herein.

FIGS. 2A, 2B, and 2C depict a second patch 200 in various views. FIG. 2A provides a top view of the second patch 200, FIG. 2B provides a bottom view of the second patch 200, and FIG. 2C provides a cross-section view of the second patch 200 taken along line B-B' in FIGS. 2A and 2B.

The second patch 200 comprises numerous features similar to features of the first patch 100. Such similar features are identified by reference numerals having the same ones and tens digits between FIGS. 1A-1C and FIGS. 2A-2C, and differing only in the hundreds digit. In other words, the element identified by reference numeral "1xx" in FIGS. 1A-1C will be similar to the element identified by reference numeral "2xx" in FIGS. 2A-2C.

For the sake of brevity, any characteristics that are the same between similar elements of the first patch 100 and the second patch 200 need not be described again. The following description of any element of the second patch 200 will be directed to differences between that element and its similar element in the first patch 100.

In the second patch 200, the coating 220 on the first surface 211 of the film 210 comprises one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, sprouted peanut extract, ginger root extract, vitamin C, and magnesium malate.

Though not to be bound by theory, the active ingredients may have the following features.

CBD is generally considered to induce calm, mitigate nausea, reduce inflammation (headaches and systemic), and assist with restful sleep. One of the main contributors to a hangover in the morning is terrible sleep at night. When the second patch 210 is worn overnight, the presence of CBD in the coating 220 may enhance recovery during sleep.

In one embodiment, the CBD is present in the form of hemp extract. In a further embodiment, the hemp extract may be essentially free of tetrahydrocannabinol (THC).

Melatonin, a hormone in the human body, has the power to induce and continue sleep. When the second patch 210 is worn overnight, melatonin, if present in the coating 220, may attack depleted glutamate stores in the liver which are responsible for disrupted sleep patterns, thereby enhancing the user's sleep throughout the night.

Dihydromyricetin (DHM) is a flavonoid extracted from the Japanese raisin tree and has been used for centuries in traditional Asian medicine as a treatment for hangovers and liver disease. DHM increases the rate of alcohol metabolism, improves the ability of the human liver enzymes to break down alcohol, reduces the amount of liver damage caused by alcohol, reduces the desire for more alcohol, and counteracts alcohol intoxication.[14] When the second patch 210 is worn overnight, DHM, if included in the coating 220, may help users avoid the feeling of waking up still intoxicated.

[14] Shen, Y. "*Dihydromyricetin As A Novel Anti-Alcohol Intoxication Medication*" Journal of Neuroscience (2012). Hase K. "*Recent Update on the Pharmacological Effects and Mechanisms of Dihydromyricetin*" Frontiers in Pharmacology (2018). https://news.usc.edu/166789/hangover-remedy-dhm-liver-protection-usc-study/

B vitamins (B1, B2, Niacin, B6, Folate, and B12) are essential for the proper metabolism of alcohol and efficient breakdown of NAC into glutathione. When the second patch 210 is worn overnight, a B vitamin complex, if included in the coating 220, may help remove the byproducts of alcohol metabolization, helping avoid hangover symptoms without a vitamin smell or taste.

Ginger is a perineal herb known as a natural motion sickness, nausea, vomiting, and stomach remedy.[15]

[15] https://www.ncbi.nlm.nih.gov/pmc/articles/PMC4818021/

Vitamin C is an essential cofactor in the enzymatic reactions (ADH and ALDH) that break down alcohol byproducts. It is essential for the proper breakdown of NAC into glutathione and also improves the effectiveness of B vitamins in controlling the accumulation of toxic alcohol metabolites.

Magnesium is an anti-stress mineral that regulates over 800 enzyme actions in the body and is depleted while drinking alcohol. Magnesium helps with hangovers by preventing thickening of blood resulting in tension headaches and pain, while also relaxing head and neck muscle tension that make them worse.[16] Malate is malic acid salt commonly used as a food additive.

[16] https://www.nutritionalmagnesium.org/magnesium-and-hangovers/

In one embodiment, the coating 220 may comprise two or more of the active ingredients.

In one embodiment, the coating 220 may comprise three or more of the active ingredients.

In one embodiment, the coating 220 may comprise four or more of the active ingredients.

In one embodiment, the coating 220 may comprise five or more of the active ingredients.

In one embodiment, the coating 220 may comprise six or more of the active ingredients.

In one embodiment, the coating 220 may comprise seven or more of the active ingredients.

In one embodiment, the coating 220 may comprise eight or more of the active ingredients.

In one embodiment, the coating 220 may comprise nine or more of the active ingredients.

In one embodiment, the coating 220 may comprise ten or more of the active ingredients.

In one embodiment, the coating 220 may comprise eleven or more of the active ingredients.

In one embodiment, the coating 220 may comprise twelve or more of the active ingredients.

In one embodiment, the coating 220 may comprise thirteen of the active ingredients.

For each active ingredient included in the coating 220, the amount of the active ingredient may be determined and adjusted as a routine matter by the person of ordinary skill in the art having the benefit of the present disclosure.

In one embodiment, the coating 220 may comprise from 3 mg to 30 mg CBD. Alternatively or in addition, the coating 220 may comprise from 1.5 mg to 15 mg glutathione. Alternatively or in addition, the coating 220 may comprise from 1 mg to 12 mg ALA. Alternatively or in addition, the coating 220 may comprise from 1.5 mg to 15 mg DHM. Alternatively or in addition, the coating 220 may comprise from 1 mg to 12 mg milk thistle extract. Alternatively or in addition, the coating 220 may comprise from 1 mg to 10 mg L-theanine. Alternatively or in addition, the coating 220 may comprise from 1 mg to 10 mg taurine. Alternatively or in addition, the coating 220 may comprise from 1.5 mg to 15 mg B vitamin complex. Alternatively or in addition, the coating 220 may comprise from 1 mg to 10 mg melatonin. Alternatively or in addition, the coating 220 may comprise from 1.5 mg to 15 mg ginger root extract. Alternatively or in addition, the coating 220 may comprise from 0.5 mg to 6 mg vitamin C. Alternatively or in addition, the coating 220 may comprise and from 0.5 mg to 6 mg magnesium malate.

In a particular embodiment, the coating may comprise 10 mg CBD. Alternatively or in addition, in this particular embodiment, the coating 220 may comprise 5 mg glutathione. Alternatively or in addition, in this particular embodiment, the coating 220 may comprise 4 mg ALA. Alternatively or in addition, in this particular embodiment, the coating 220 may comprise 5 mg DHM. Alternatively or in addition, in this particular embodiment, the coating 220 may comprise 4 mg milk thistle extract. Alternatively or in addition, in this particular embodiment, the coating 220 may comprise 3 mg L-theanine. Alternatively or in addition, in this particular embodiment, the coating 220 may comprise 3 mg taurine. Alternatively or in addition, in this particular embodiment, the coating 220 may comprise 6 mg B vitamin complex. Alternatively or in addition, in this particular embodiment, the coating 220 may comprise 3 mg melatonin. Alternatively or in addition, in this particular embodiment, the coating 220 may comprise 5 mg ginger root extract. Alternatively or in addition, in this particular embodiment, the coating 220 may comprise 2 mg vitamin C. Alternatively or in addition, in this particular embodiment, the coating 220 may comprise and 2 mg magnesium malate.

In the B vitamin complex, the relative proportions of B1, B2, niacin, B6, folate, and B12 may be selected as a routine matter for the person of ordinary skill in the art having the benefit of the present disclosure.

Figure 3:
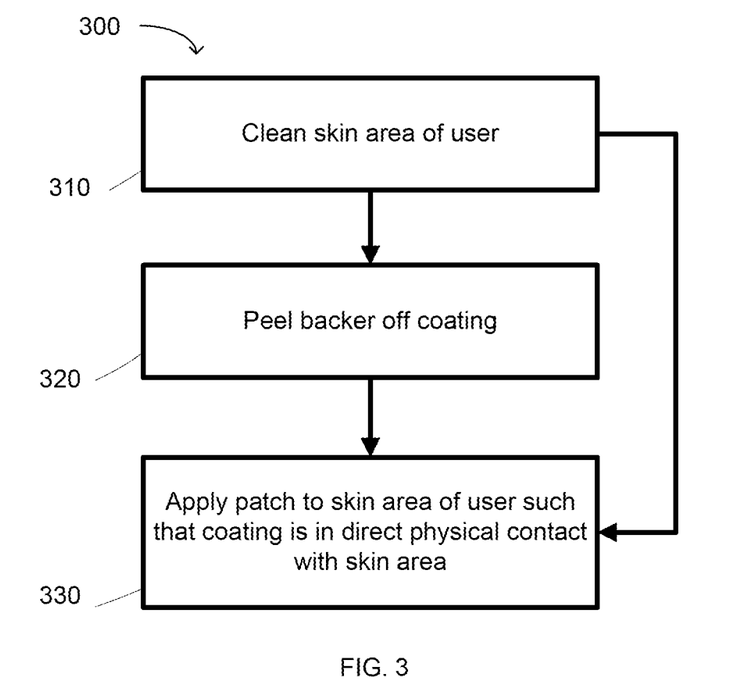
FIG. 3 is a flowchart of a first method, in accordance with embodiments herein.

FIG. 3 is a flowchart of a first method 300, in accordance with embodiments herein. The first method 300 comprises applying (at 330), to a skin area of a user, a patch comprising a film having a first surface and a second surface, wherein the second surface is opposed to the first surface, and a coating on the first surface of the film, such that the coating is in direct physical contact with the skin area after the applying.

The coating comprises a transdermal adhesive.

In one embodiment, the coating comprises one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract. A coating comprising one or more active ingredients selected from the group set forth in this paragraph may be termed a "first coating."

In another embodiment, the coating comprises one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, sprouted peanut extract, ginger root extract, vitamin C, and magnesium malate. A coating comprising one or more active ingredients selected from the group set forth in this paragraph may be termed a "second coating."

Applying (at 330) may be performed to any skin area of the user. In one embodiment, the skin area is an area in which one or more veins are in proximity to the skin. The skin area may be a relatively hairless part of the body. In one embodiment, the skin area may be an inside of a wrist, a top of a foot, or a back of a shoulder.

In one embodiment, wherein the coating is a first coating, applying (at 330) may be performed before the user consumes a significant amount of alcohol. For example, applying (at 330) may be performed up to about one hour prior to the user consuming his or her first alcoholic beverage of the day. After applying (at 330) a patch comprising the first coating, the patch may be kept on the user's skin area for up to about ten hours.

In another embodiment, wherein the coating is a second coating, applying (at 330) may be performed after the user consumes a significant amount of alcohol and prior to the user attempting to sleep. After applying (at 330) a patch comprising the second coating, the patch may be kept on the user's skin area overnight, e.g., for up to about ten hours or until the user wakes.

The first method 300 may optionally comprise one or more other actions. In one embodiment, the first method 300 may further comprise cleaning (at 310) the skin area of the user prior to applying the patch. Cleaning (at 310) may be performed by any topical skin cleaner, such as soapy water, isopropanol, etc. Cleaning (at 310) with isopropanol in an aqueous solution of 80% or higher may combine convenient cleaning with minimal residue of soap or water, either of which may impair adhesion of the transdermal adhesive in the patch coating with the skin.

Alternatively or in addition, in embodiments wherein the patch may further comprise a backer on the coating, the first method 300 may comprise peeling (at 320) the backer off the coating prior to applying the patch. "Peeling" is used for convenience; other techniques that lead to removal of the backer are encompassed by the term, even if the backer is not removed by delaminating the backer from the coating starting at a particular location or locations.

In one embodiment, the present disclosure relates to a kit, comprising a patch comprising a film having a first surface and a second surface, wherein the second surface is opposed to the first surface, and a first coating or a second coating on the first surface of the film; and instructions to perform the first method 300, i.e., instructions to apply, to a skin area of a user, the patch, such that the coating is in direct physical contact with the skin area after the applying.

In embodiments wherein the coating of the patch is a first coating, the instructions to apply the patch may further comprise instructions to apply the patch prior to consumption of alcohol by the user. In a further embodiment, the instructions to apply the patch prior to consumption of alcohol may further comprise instructions to apply the patch about one hour before consumption of alcohol by the user.

In embodiments wherein the coating of the patch is a second coating, the instructions to apply the patch may further comprise instructions to apply the patch after the user has ceased consuming alcohol and/or when the user intends to go to sleep for the night. In a further embodiment, the instructions to apply the patch after consumption alcohol may further comprise instructions to apply the patch about one hour or less before the user attempts to sleep. In another further embodiment, the instructions to apply the patch when the user intends to go to sleep may further comprise instructions to apply the patch about one hour or less before the user attempts to sleep.

The kit may further comprise instructions to clean the skin area of the user prior to applying the patch. In this embodiment, the kit may further comprise a skin-cleaning product. For example, the skin-cleaning product may be a wipe comprising isopropanol, among other skin-cleaning products that will be apparent to the person of ordinary skill in the art having the benefit of the present disclosure.

Alternatively or in addition, in embodiments wherein the patch further comprises a backer on the coating, the kit may further comprise instructions to peel the backer off the coating prior to applying the patch.

Figure 4:
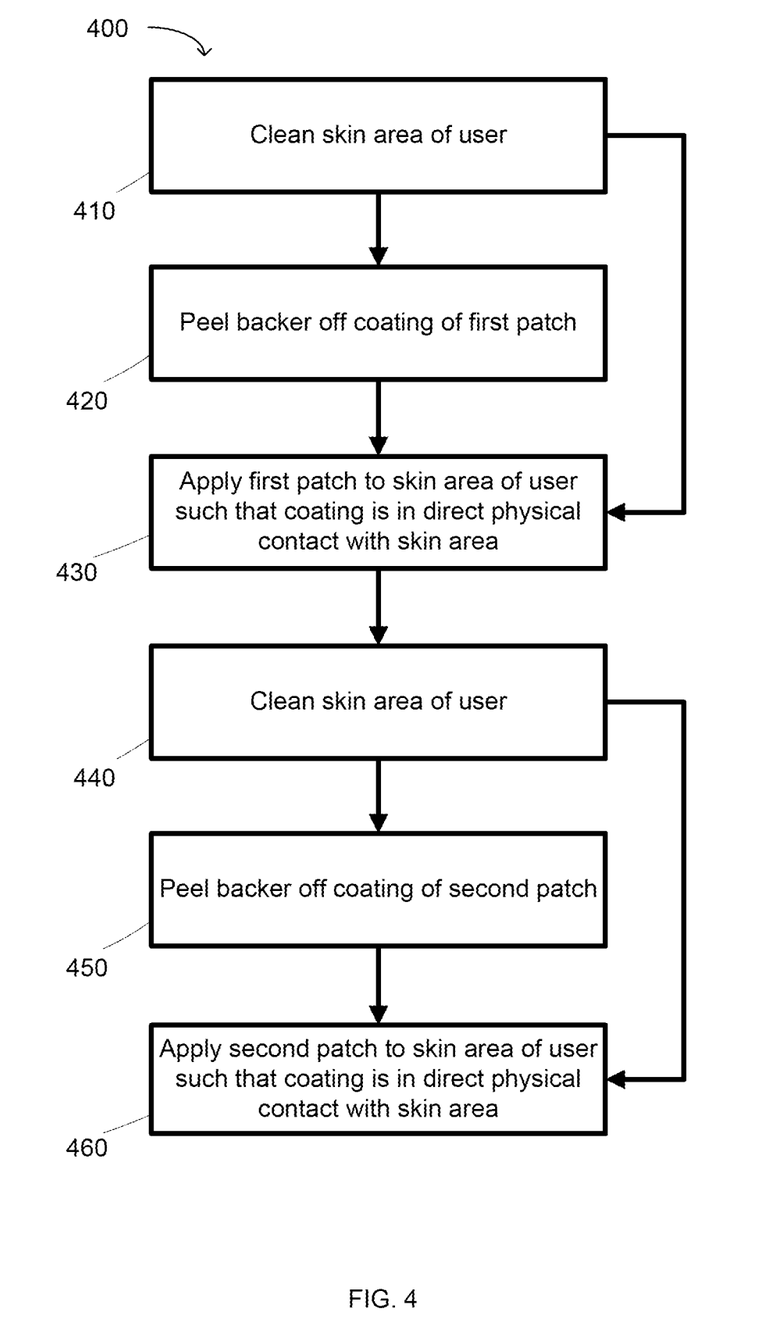
FIG. 4 is a flowchart of a second method, in accordance with embodiments herein.

FIG. 4 is a flowchart of a second method 400, in accordance with embodiments herein. The second method 400 comprises applying (at 430), to a skin area of a user, a first patch comprising a film having a first surface and a second surface, wherein the second surface is opposed to the first surface, and a coating on the first surface of the film, wherein the coating comprises a transdermal adhesive and one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract; such that the coating is in direct physical contact with the skin area after the applying.

The second method 400 also comprises applying (at 460), to the same or a different skin area of the user after applying the first patch, a second patch comprising a film having a first surface and a second surface, wherein the second surface is opposed to the first surface, and a coating on the first surface of the film, wherein the coating comprises a transdermal adhesive and one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, sprouted peanut extract, ginger root extract, vitamin C, and magnesium malate; such that the coating is in direct physical contact with the skin area after the applying.

Desirably, the applying (at 430) the first patch may be performed before the user consumes alcoholic beverages, and the applying (at 460) the second patch may be performed after the user ceased consumption of alcoholic beverages for the day and prior to the user attempting to sleep.

The second method 400 may also comprise any or all of the following further actions: cleaning (at 410) the skin area of the user prior to applying the first patch; in embodiments wherein the first patch further comprises a backer on the coating, peeling (at 420) the backer off the coating prior to applying the first patch; cleaning (at 440a0 the skin area of the user prior to applying the second patch; and in embodiments wherein the second patch further comprises a backer on the coating, peeling (at 450a0 the backer off the coating prior to applying the second patch.

Figure 5:
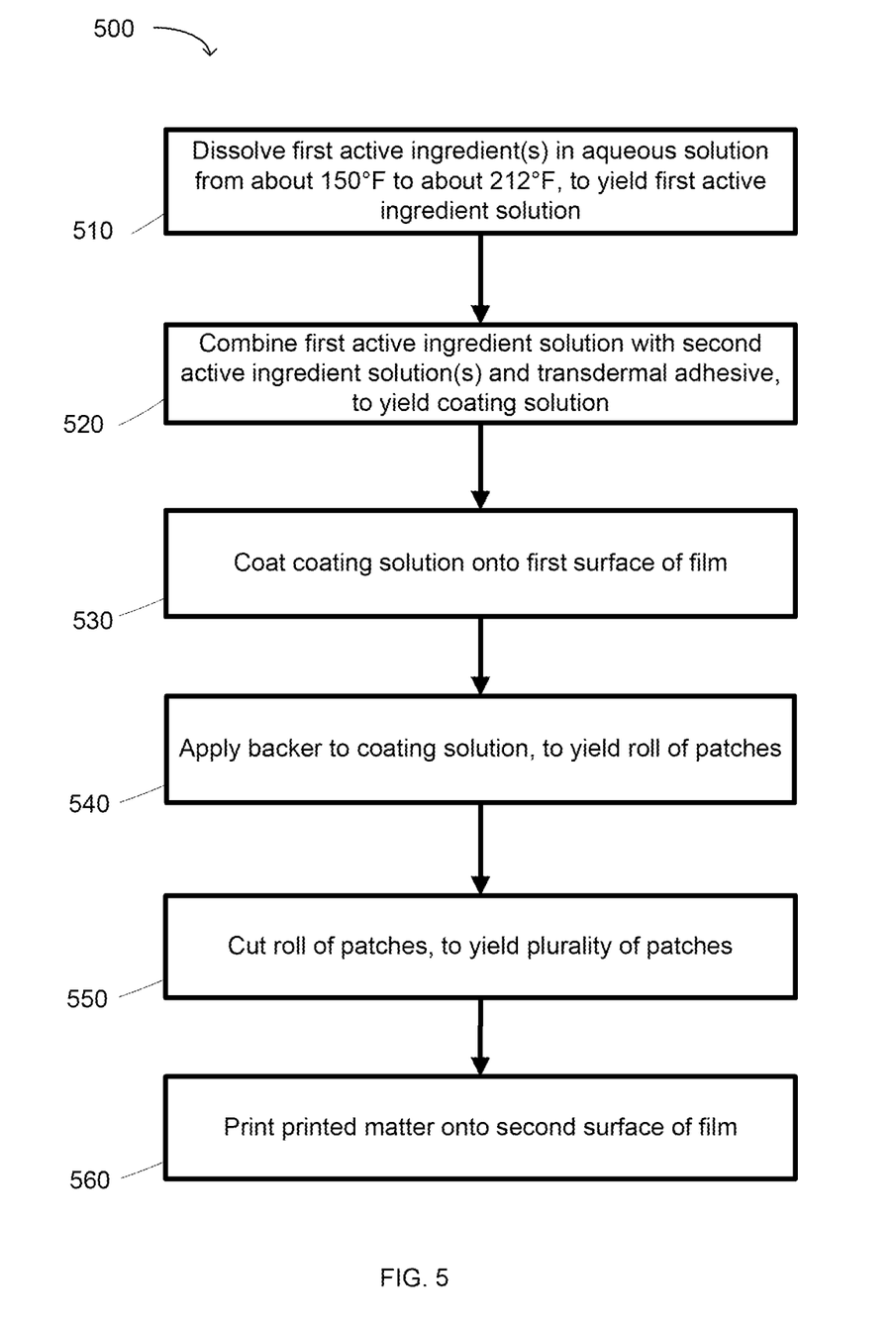
FIG. 5 is a flowchart of a third method, in accordance with embodiments herein.

FIG. 5 is a flowchart of a third method 500, in accordance with embodiments herein. The third method 500 comprises dissolving (at 510), in an aqueous solution with a temperature from about 150° F. (about 65° C.) to about 212° F. (about 100° C.), one or more first active ingredients, to yield a first active ingredient solution.

In one embodiment, the one or more first active ingredients may be selected from the group consisting of glutathione, N-acetyl cysteine (NAC), L-cysteine, alpha lipoic acid (ALA), and L-theanine, taurine, and quercetin. In this embodiment, the first active ingredient solution may be termed a "pre" first active ingredient solution. "Pre" here refers to the expected use of the first active ingredient(s) in a first patch intended for use prior to consumption of alcohol by a consumer.

Alternatively, in one embodiment, the one or more first active ingredients may be selected from the group consisting of cannabidiol (CBD), glutathione, alpha lipoic acid (ALA), dihydromyricetin (DHM), L-theanine, taurine, a B vitamin complex, melatonin, sprouted peanut extract, vitamin C, and magnesium malate. In this embodiment, the first active ingredient solution may be termed a "post" first active ingredient solution. "Post" here refers to the expected use of the first active ingredient(s) in a second patch intended for use after consumption of alcohol by a consumer.

Subsequently, the third method 500 comprises combining (at 520) the first active ingredient solution with (a) one or more second active ingredient solutions and (b) a transdermal adhesive, to yield a coating solution.

In embodiments wherein the method is performed with the "pre" first active ingredient solution, the second active ingredient solution(s) may be selected from the group consisting of milk thistle extract, sweet lime extract, Korean pear extract, sprouted peanut extract, and prickly pear extract. The coating solution resulting from combining the "pre" first active ingredient solution with the second active ingredient solution(s) of this paragraph may be termed a "pre" coating solution.

Alternatively, in embodiments wherein the method is performed with the "post" first active ingredient solution, the second active ingredient solution(s) may be selected from the group consisting of milk thistle extract and ginger root extract. The coating solution resulting from combining the "post" first active ingredient solution with the second active ingredient solution(s) of this paragraph may be termed a "post" coating solution.

The third method 500 also comprises coating (at 530) the coating solution onto a first surface of a film, wherein the film has a first surface and a second surface, wherein the second surface is opposed to the first surface. The film may be clear FT-200 polyethylene with a thickness of 0.102 mm, among other possibilities that will be apparent to the person of ordinary skill in the art having the benefit of the present disclosure. At this stage, the film may have any desired width. In one embodiment, the film may have a width of about 1050 mm, though numerous other widths are possible and may routinely selected in view of the manufacturing equipment available and other parameters apparent to the person of ordinary skill in the art having the benefit of the present disclosure.

The amounts of the various active ingredients formulated into the coating solution, and the density of the coating solution in units of mass or volume per area of the first surface of the film, may be chosen by the person of ordinary skill in the art in view of the discussion of component amounts per patch, given above, and further in view of the manufacturing process.

The third method 500 also comprises applying (at 540) a backer to the coating solution, to yield a roll of patches. In embodiments, before, during, or after the applying (at 540), the film may be further cut to yield a plurality of rolls of patches, such that each of the plurality of rolls of patches has a width of about 128 mm. Other widths of the roll of patches may be routinely determined and used by the person of ordinary skill in the art having the benefit of the present disclosure.

In one embodiment, the rolls of patches may be allowed to sit for a period of time, such as about 24 hr., before subsequent actions are performed.

Regardless of the width of each roll of patches, the third method 500 additionally comprises cutting (at 550) the roll of patches, to yield a plurality of patches. Each patch may have a uniform size desired for a single use of the "pre" or "post" coated-patch. In one embodiment, each patch may have a surface area (i.e., width×height, ignoring thickness) of about 45 mm×45 mm (about 1¾ inches by about 1¾ inches). Numerous other sizes of the patches may be produced. Not all the patches need have the same surface area.

In one embodiment, the third method 500 may further comprise printing (at 560) a printed matter on the second surface of the film, wherein the printed matter comprises an ink which is substantially opaque at a temperature below about 80° F. (about 27° C.) and which is substantially transparent at a temperature above about 95° F. (about 35° C.). The printed matter may be the manufacturer's logo, an advertisement, etc.

The printing (at 560) may be performed at any time during the third method 500 deemed fit by the person of ordinary skill in the art having the benefit of the present disclosure. In one embodiment, the printing (at 560) is performed substantially simultaneously with the cutting.

Whether or not printing (at 560) is performed, each of the plurality of patches may then be counted, shrink-wrapped, labeled, packed, and subsequently entered into commerce.

In particular embodiments, the present disclosure may relate to one or more of the following numbered paragraphs.

201. A method, comprising:
applying, to a skin area of a user, a patch comprising a film having a first surface and a second surface, wherein the second surface is opposed to the first surface, and a coating on the first surface of the film, wherein the coating comprises a transdermal adhesive and one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract;
such that the coating is in direct physical contact with the skin area after the applying.

202. The method of claim 201, further comprising:
cleaning the skin area of the user prior to applying the patch.

203. The method of claim 201, wherein the patch further comprises a backer on the coating, and the method further comprises:
peeling the backer off the coating prior to applying the patch.

301. A method, comprising:
applying, to a skin area of a user, a patch comprising a film having a first surface and a second surface, wherein the second surface is opposed to the first surface, and a coating on the first surface of the film, wherein the coating comprises a transdermal adhesive and one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, ginger root extract, vitamin C, and magnesium malate;
such that the coating is in direct physical contact with the skin area after the applying.

302. The method of claim 301, further comprising:
cleaning the skin area of the user prior to applying the patch.

303. The method of claim 301, wherein the patch further comprises a backer on the coating, and the method further comprises:
peeling the backer off the coating prior to applying the patch.

401. A kit, comprising:
a patch comprising a film having a first surface and a second surface, wherein the second surface is opposed to the first surface, and a coating on the first surface of the film, wherein the coating comprises a transdermal adhesive and one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract; and
instructions to:
apply, to a skin area of a user, the patch, such that the coating is in direct physical contact with the skin area after the applying.

402. The kit of claim 401, further comprising instructions to:
clean the skin area of the user prior to applying the patch.

403. The kit of claim 402, further comprising:
a skin-cleaning product.

404. The kit of claim 401, wherein the patch further comprises a backer on the coating, and the kit further comprises instructions to:
peel the backer off the coating prior to applying the patch.

405. The kit of claim 401, wherein the instructions to apply the patch further comprise instructions to apply the patch prior to consumption of alcohol by the user.

406. The kit of claim 405, wherein the instructions to apply the patch prior to consumption of alcohol further comprise instructions to apply the patch about one hour before consumption of alcohol by the user.

501. A kit, comprising:
a patch comprising a film having a first surface and a second surface, wherein the second surface is opposed to the first surface, and a coating on the first surface of the film, wherein the coating comprises a transdermal adhesive and one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, sprouted peanut extract, ginger root extract, vitamin C, and magnesium malate; and
instructions to:
apply, to a skin area of a user, the patch, such that the coating is in direct physical contact with the skin area after the applying.

502. The kit of claim 501, further comprising instructions to:
clean the skin area of the user prior to applying the patch.

503. The kit of claim 502, further comprising:
a skin-cleaning product.

504. The kit of claim 501, wherein the patch further comprises a backer on the coating, and the kit further comprises instructions to:
peel the backer off the coating prior to applying the patch.

505. The kit of claim 501, wherein the instructions to apply the patch further comprise instructions to apply the patch after consumption of alcohol by the user and prior to the user falling asleep.

601. A method, comprising:
applying, to a skin area of a user, a first patch comprising a film having a first surface and a second surface, wherein the second surface is opposed to the first surface, and a coating on the first surface of the film, wherein the coating comprises a transdermal adhesive and one or more active ingredients selected from the group consisting of glutathione, N-acetyl cysteine (NAC), L-cysteine, alpha lipoic acid (ALA), milk thistle extract, L-theanine, taurine, quercetin, sweet lime extract, Korean pear extract, sprouted peanut extract, and prickly pear extract; such that the coating is in direct physical contact with the skin area after the applying; and
applying, to the same or a different skin area of the user after applying the first patch, a second patch comprising a film having a first surface and a second surface, wherein the second surface is opposed to the first surface, and a coating on the first surface of the film, wherein the coating comprises a transdermal adhesive and one or more active ingredients selected from the group consisting of cannabidiol (CBD), glutathione, alpha lipoic acid (ALA), dihydromyricetin (DHM), milk thistle extract, L-theanine, taurine, a B vitamin complex, melatonin, sprouted peanut extract, ginger root extract, vitamin C, and magnesium malate; such that the coating is in direct physical contact with the skin area after the applying.

602. The method of claim 601, further comprising:
cleaning the skin area of the user prior to applying the first patch.

603. The method of claim 601, wherein the first patch further comprises a backer on the coating, and the method further comprises:
peeling the backer off the coating prior to applying the first patch.

604. The method of claim 601, further comprising:
cleaning the skin area of the user prior to applying the second patch.

605. The method of claim 601, wherein the second patch further comprises a backer on the coating, and the method further comprises:
peeling the backer off the coating prior to applying the second patch.

701. A method, comprising:
dissolving, in an aqueous solution with a temperature from about 150° F. (about 65° C.) to about 212° F. (about 100° C.), one or more first active ingredients selected from the group consisting of glutathione, N-acetyl cysteine (NAC), L-cysteine, alpha lipoic acid (ALA), and L-theanine, taurine, and quercetin, to yield a first active ingredient solution;
combining the first active ingredient solution with (a) one or more second active ingredient solutions selected from the group consisting of milk thistle extract, sweet lime extract, Korean pear extract, sprouted peanut extract, and prickly pear extract, and (b) a transdermal adhesive, to yield a coating solution;
coating the coating solution onto a first surface of a film, wherein the film has a first surface and a second surface, wherein the second surface is opposed to the first surface;
applying a backer to the coating solution, to yield a roll of patches; and
cutting the roll of patches, to yield a plurality of patches.

702. The method of claim 701, further comprising:
printing a printed matter on the second surface of the film, wherein the printed matter comprises an ink which is substantially opaque at a temperature below about 80° F. (about 27° C.) and which is substantially transparent at a temperature above about 95° F. (about 35° C.).

703. The method of claim 702, wherein the printing is performed substantially simultaneously with the cutting.

801. A method, comprising:
dissolving, in an aqueous solution with a temperature from about 150° F. (about 65° C.) to about 212° F. (about 100° C.), one or more first active ingredients selected from the group consisting of cannabidiol (CBD), glutathione, alpha lipoic acid (ALA), dihydromyricetin (DHM), L-theanine, taurine, a B vitamin complex, melatonin, vitamin C, and magnesium malate, to yield a first active ingredient solution;
combining the first active ingredient solution with (a) one or more second active ingredient solutions selected from the group consisting of milk thistle extract, sprouted peanut extract, and ginger root extract, and (b) a transdermal adhesive, to yield a coating solution;
coating the coating solution onto a first surface of a film, wherein the film has a first surface and a second surface, wherein the second surface is opposed to the first surface;
applying a backer to the coating solution, to yield a roll of patches; and
cutting the roll of patches, to yield a plurality of patches.

802. The method of claim 801, further comprising:
printing a printed matter on the second surface of the film, wherein the printed matter comprises an ink which is substantially opaque at a temperature below about 80° F. (about 27° C.) and which is substantially transparent at a temperature above about 95° F. (about 35° C.).

803. The method of claim 802, wherein the printing is performed substantially simultaneously with the cutting.

The particular embodiments disclosed above are illustrative only, as the disclosure may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is, therefore, evident that the particular embodiments disclosed above may be altered or modified and all such variations are considered within the scope and spirit of the disclosure. Accordingly, the protection sought is as set forth in the claims below.

What is claimed is:

1. A patch, comprising:
a film having a first surface and a second surface, wherein the second surface is opposed to the first surface, and
a coating on the first surface of the film, wherein the coating comprises a transdermal adhesive and eight or more active ingredients selected from the group consisting of from 3 mg to 30 mg glutathione, from 2 mg to 20 mg L-cysteine, from 2 mg to 20 mg alpha lipoic acid (ALA), from 2 mg to 20 mg milk thistle extract, from 1.5 mg to 15 mg L-theanine, from 2 mg to 20 mg taurine, from 1.5 mg to 15 mg quercetin, from 0.5 mg to 6 mg sweet lime extract, from 0.5 mg to 6 mg Korean pear extract, and from 0.5 mg to 6 mg prickly pear extract.

2. The patch of claim 1, wherein the coating comprises 10 mg glutathione, 6 mg L-cysteine, 6 mg ALA, 6 mg milk thistle extract, 5 mg L-theanine, 6 mg taurine, 5 mg quercetin, 2 mg sweet lime extract, 2 mg Korean pear extract, and 2 mg prickly pear extract.

3. A patch, comprising:
a film having a first surface and a second surface, wherein the second surface is opposed to the first surface, and
a coating on the first surface of the film, wherein the coating comprises a transdermal adhesive and eight or more active ingredients selected from the group consisting of from 3 mg to 30 mg cannabidiol (CBD), from 1.5 mg to 15 mg glutathione, from 1 mg to 12 mg alpha lipoic acid (ALA), from 1.5 mg to 15 mg dihydromyricetin (DHM), from 1 mg to 12 mg milk thistle extract, from 1 mg to 10 mg L-theanine, from 1 mg to 10 mg taurine, from 1.5 mg to 15 mg B vitamin complex, from 1 mg to 10 mg melatonin, from 1.5 mg to 15 mg ginger root extract, from 0.5 mg to 6 mg vitamin C, and from 0.5 mg to 6 mg magnesium malate.

4. The patch of claim 3, wherein the coating comprises 10 mg CBD, 5 mg glutathione, 4 mg ALA, 5 mg DHM, 4 mg milk thistle extract, 3 mg L-theanine, 3 mg taurine, 6 mg B vitamin complex, 3 mg melatonin, 5 mg ginger root extract, 2 mg vitamin C, and 2 mg magnesium malate.

* * * * *